US008236941B2

(12) United States Patent
Yao

(10) Patent No.: US 8,236,941 B2
(45) Date of Patent: Aug. 7, 2012

(54) TETRACYCLINE REPRESSOR REGULATED ONCOLYTIC VIRUSES

(75) Inventor: Feng Yao, Needham, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 378 days.

(21) Appl. No.: 12/553,051

(22) Filed: Sep. 2, 2009

(65) Prior Publication Data
US 2010/0015687 A1 Jan. 21, 2010

Related U.S. Application Data

(62) Division of application No. 11/822,373, filed on Jul. 5, 2007, now abandoned.

(60) Provisional application No. 60/819,382, filed on Jul. 10, 2006.

(51) Int. Cl.
C07H 21/04 (2006.01)
C12N 15/79 (2006.01)
(52) U.S. Cl. .................... 536/24.1; 536/24.5; 435/320.1
(58) Field of Classification Search .................. None
See application file for complete search history.

(56) References Cited

U.S. PATENT DOCUMENTS

| 5,464,758 | A | 11/1995 | Gossen |
| 5,589,362 | A | 12/1996 | Bujard |
| 5,917,122 | A | 6/1999 | Byrne |
| 5,965,440 | A | 10/1999 | Reeves |
| 5,972,650 | A | 10/1999 | Yao |
| 6,251,640 | B1 | 6/2001 | Yao |
| 6,261,552 | B1 | 7/2001 | DeLuca |
| 6,444,871 | B1 | 9/2002 | Yao |
| 2003/0113348 | A1 | 6/2003 | Coffin |
| 2004/0063094 | A1 | 4/2004 | Coffin et al. |
| 2005/0266564 | A1 | 12/2005 | Yao |
| 2006/0116340 | A1* | 6/2006 | Lewin et al. ............... 514/44 |

FOREIGN PATENT DOCUMENTS

| WO | WO 2011/025717 A2 | 3/2011 |
| WO | WO 2011/079073 A2 | 6/2011 |

OTHER PUBLICATIONS

Office Action mailed Aug. 16, 2011 in the prosecution of U.S. Appl. No. 11/117,375.
Response to Office Action of Nov. 9, 2009 in the prosecution of U.S. Appl. No. 11/117,375, filed by Applicant with RCE on Feb. 10, 2010.
Office Action mailed Aug. 5, 2010 in the prosecution of U.S. Appl. No. 11/117,375 along with claims under consideration in the Office Action.
Response to Office Action of Aug. 5, 2010 in the prosecution of U.S. Appl. No. 11/117,375, filed by Applicant on Nov. 10, 2010.
Office Action mailed Jan. 20, 2011 in the prosecution of U.S. Appl. No. 11/117,375.
Berens, et al., "Gene regulation by tetracyclines: Constraints of resistance regulation in bacteria shape TetR for application in eukaryotes," Eur. J. Biochem. 270:3109-3121 (2003).
Corbel, et al., "Latest developments and in vivo use of the Tet system: ex vivo and in vivo delivery of tetracycline-regulated genes," Current Opinion in Biotechnology 13:448-452 (2002).
Martinez, et al., "The Conserved Helicase Motifs of the Herpes Simplex Virus Type 1 Origin-Binding Protein UL9 Are Important for Function," Journal of Virology 66(11):6735-6746 (Nov. 1992).
Office Action mailed Jun. 12, 2007 in the prosecution of U.S. Appl. No. 11/117,375 along with claims under consideration in the Office Action.
Response to Office Action of Jun. 12, 2007 in the prosecution of U.S. Appl. No. 11/117,375, filed by Applicant on Sep. 12, 2007.
Office Action mailed Nov. 27, 2007 in the prosecution of U.S. Appl. No. 11/117,375 along with claims under consideration in the Office Action.
Response to Office Action of Nov. 27, 2007 in the prosecution of U.S. Appl. No. 11/117,375, filed by Applicant on Feb. 24, 2008.
Appeal Brief filed by Applicant on May 27, 2008 in the prosecution of U.S. Appl. No. 11/117,375.
Office Action mailed Oct. 15, 2008 in the prosecution of U.S. Appl. No. 11/117,375 along with claims under consideration in the Office Action.
Response to Office Action of Oct. 15, 2008 in the prosecution of U.S. Appl. No. 11/117,375, filed by Applicant on Feb. 24, 2008.
Notice of Noncompliant Amendment mailed Apr. 21, 2009 in the prosecution of U.S. Appl. No. 11/117,375.
Response to Notice of Noncompliant Amendment of Apr. 21, 2009 in the prosecution of U.S. Appl. No. 11/117,375, filed by Applicant on May 4, 2009.
Office Action mailed Nov. 9, 2009 in the prosecution of U.S. Appl. No. 11/117,375 along with claims under consideration in the Office Action.
Koelle, et al., "Herpes Simplex Virus Infection of Human Fibroblasts and Keratinocytes Inhibits Recognition by Cloned CD8+ Cytotoxic T Lymphocytes," J. Clin. Invest. 91:961-968 (Mar. 1993).
Kousoulas, et al., "Antibody-Resistant Mutations in Cross-Reactive and Type-Specific Epitopes of Herpes Simplex Virus 1 Glycoprotein B Map in Separate Domains," Virology 166:423-431 (1988).
Lakeman, et al., "Analysis of DNA From Recurrent Genital Herpes Simplex Virus Isolates by Restriction Endonuclease Digestion," Sex. Transm. Dis. 13:61-66 (1986).
Leib, et al , "Immediate-Early Regulatory Gene Mutants Define Different Stages in the Establishment and Reactivation of Herpes Simplex Virus Latency," J. Virol. 63(2):759-768 (Feb. 1989).
Lewandowski, et al., "Evidence that deficient IFN-γ production is a biological basis of herpes simplex virus type-2 neurovirulence," J. Neuroimmunol. 81:66-75 (1998).
Liesegang, "Herpes Simplex Virus Epidemiology and Ocular Importance," Cornea 20(1):1-13 (2001).
Looker, et al., "A systematic review of the epidemiology and interaction of herpes simplex virus types 1 and 2," Sex. Transm. Infect. 81:103-107 (2005).

(Continued)

Primary Examiner — Michael Burkhart
(74) Attorney, Agent, or Firm — Law Office of: Michael A. Sanzo, LLC

(57) ABSTRACT

The present invention is directed oncolytic Herpes simplex-1 viruses whose replication is controlled using a tetracycline operator/repressor system. The invention also includes DNA sequences used in making the viruses and methods in which these viruses are used in the treatment of cancer patients with solid tumors.

20 Claims, No Drawings

OTHER PUBLICATIONS

Lu, et al., "High Level Expression of Glycoprotein D by a Dominant-Negative IISV-1 Virus Augments its Efficacy as a Vaccine against HSV-1 Infection," *J. Invest. Dermatol.* 129:1174-1184 (2009).

McGeoch, et al., "DNA sequence of the region in the genome of herpes simplex virus type 1 containing the exonuclease and neighbouring genes," *Nucl. Acid Res.* 14(8):3435-48 (1986).

Mertz, et al., "Risk Factors for the Sexual Transmission of Genital Herpes," *Ann. Intern. Med.* 116:197-202 (1992).

Mikloska, et al., "Herpes simplex virus type 1 glycoproteins gB, gC and gD are major targets for CD4 T-lymphocyte cytotoxicity in HLA-DR expressing human epidermal keratinocytes," *J. gen. Virol.* 79:353-361 (1998).

Mikloska, et al., "Monophosphoryl Lipid A and QS21 Increase CD8 T Lymphocyte Cytotoxicity to Herpes Simplex Virus-2 Infected Cell Proteins 4 and 27 Through IFN-1γ and IL-12 Production," *J. Immunol.* 164:5167-5176 (2000).

Minson, et al., "An Analysis of the Biological Properties of Monoclonal Antibodies against Glycoprotein D of Herpes Simplex Virus and Identification of Amino Acid Substitutions that Confer Resistance to Neutralization," *J. gen. Virol.* 67:1001-1013 (1986).

Morrison, et al., "Influence of Mucosal and Parenteral Immunization with a Replication-Defective Mutant of HSV-2 on Immune Responses and Protection from Genital Challenge," *Virology* 243:178-187 (1998).

Muller, "Binding of the Herpes Simplex Virus Immediate-Early Gene Product ICP4 to Its Own Transcription Start Site," *J. Virol.* 61(3):858-865 (Mar. 1987).

Nagot, et al., "Reduction of HIV-1 RNA Levels with Therapy to Suppress Herpes Simplex Virus," *N. Engl. J. Med.* 356(8):790-799 (Feb. 2007).

Para, et al., "Potent Neutralizing Activity Associated with Anti-Glycoprotein D Specificity Among Monoclonal Antibodies Selected for Binding to Herpes Simplex Virions," *J. Virol.* 55(2):483-488 (Aug. 1985).

Pereira, "Use of monoclonal antibodies to HSV-1 and HSV-2 for serological analysis of the viral glycoproteins," *Dev. Biol. Stand.* 52:115-131 (1982).

Pereira, et al., "Type-Common and Type-Specific Monoclonal Antibody to Herpes Simplex Virus Type 1," *Infect. Immun.* 29(2):724-732 (Aug. 1980).

Roberts, et al., "Direct Correlation between a Negative Autoregulatory Response Element at the Cap Site of the Herpes Simplex Virus Type 1 IE175 (α4) Promoter and a Specific Binding Site for the IE175 (ICP4) Protein," *J. Virol.* 62(11):4307-4320 (Nov. 1988).

Roizman, et al., "Herpes Simplex Viruses and Their Replication," Chapter 72, pp. 2399-2459; D.M. Knipe (ed.), Fields Virology, 4$^{th}$ ed. Lippincott Williams & Wilkins, Philadelphia, PA. (2001).

Schmidt, et al., "Reinfection is an Uncommon Occurrence in Patients with Symptomatic Recurrent Genital Herpes," *J. Infect. Dis.* 149(4):645-646 (Apr. 1984).

Stanberry, "Clinical Trials of Prophylactic and Therapeutic Herpes Simplex Virus Vaccines," *Herpes* 11(Suppl 3):161A-169A (2004).

Stanberry, et al., "Prospects for Control of Herpes Simplex Virus Disease through Immunization," *Clin. Infect. Dis.* 30:549-566 (2000).

Stanberry, et al., "Glycoprotein-D-Adjuvant Vaccine to Prevent Genital Herpes," *N. Engl. J Med.* 347(21):1652-1661 (Nov. 2002).

Starr, et al., "Long-term persistence of defective HSV-1 vectors in the rat brain is demonstrated by reactivation of vector gene expression," *Gene Ther.* 3:615-623 (1996).

Stow, et al., "Isolation and Characterization of a Herpes Simplex Virus Type 1 Mutant Containing a Deletion within the Gene Encoding the Immediate Early Polypeptide Vmw110," *J. gen. Virol.* 67:2571-2585 (1986).

Tigges, et al., "Human CD8$^+$ Herpes Simplex Virus-Specific Cytotoxic T-Lymphocyte Clones Recognize Diverse Virion Protein Antigens," *J. Virol.* 66(3):1622-1634 (Mar. 1992).

Whitley, et al., "Herpes Simplex Viruses," *Clin. Infect. Dis.* 26:541-53; quiz 554-55 (1998).

Xu, et al., "Seroprevalence and Coinfection with Herpes Simplex Virus Type 1 and Type 2 in the United States, 1988-1994," *J. Infect. Dis.* 185:1019-1024 (2002).

Yao, et al., "A Novel Anti-Herpes Simplex Virus Type 1-Specific Herpes Simplex Virus Type 1 Recombinant," *Hum. Gene Ther.* 10:1811-1818 (Jul. 1999).

Yao, et al., "A Novel Tetracycline-Inducible Viral Replication Switch," *Hum. Gene Ther.* 10:419-427 (Feb. 1999).

Yao, et al., "Inhibition of herpes simplex virus type 2 (HSV-2) viral replication by the dominant negative mutant polypeptide of IISV-1 origin binding protein," *Antiviral Res.* 53:127-33 (2002).

Zarling, et al., "Human Cytotoxic T Cell Clones Directed Against Herpes Simplex Virus-Infected Cells," *J. Immunol.* 136(12):4669-4673 (Jun. 1986).

Response to Office Action of Jan. 20, 2011 filed in the prosecution of U.S. Appl. No. 11/117,375 on May 20, 2011 along with an RCE.

Declaration Under 37 CFR §1.132 filed in the prosecution of U.S. Appl. No. 11/117,375 on May 20, 2011.

Abu-Raddad, et al., "Genital Herpes Has Played a More Important Role than Any Other Sexually Transmitted Infection in Driving HIV Prevalence in Africa," *PLoS ONE* 3(5)(e2230):1-15 (May 2008).

Ackermann, et al., "Characterization of Herpes Simplex Virus 1 α Proteins, 0, 4, and 27 with Monoclonal Antibodies," *J. Virol.* 52(1):108-118 (Oct. 1984).

Adelson, et al., "Simultaneous detection of herpes simplex virus types 1 and 2 by real-time PCR and Pyrosequencing," *J. Clin. Virol.* 33:25-34 (2005).

Akhrameyeva, et al., "Development of a Glycoprotein D-Expressing Dominant-Negative and Replication-Defective Herpes Simplex Virus 2 (IISV-2) Recombinant Viral Vaccine against IISV-2 Infection in Mice," *J. Virol.* 85 (10):5036-5047 (May 2011).

Arvin, et al., "Detection of Type-Specific Antibody to Herpes Simplex Virus Type 1 by Radioimmunoassay with Herpes Simples Virus Type 1 Glycoprotein C Purified with Monoclonal Antibody," *Infect. Immun.* 40(1):184-189 (1983).

Augustinova, et al., "The Dominant-Negative Herpes Simplex Virus Type 1 (HSV-1) Recombinant CJ83193 Can Serve as an Effective Vaccine against Wild-Type HSV-1 Infection in Mice," *J. Virol.* 78(11):5756-5765 (Jun. 2004).

Bourne, et al., "DNA immunization confers protective immunity on mice challenged intravaginally with herpes simplex virus type 2," *Vaccine* 14(13):1230-1234 (1996).

Brans, et al., "Prevention of Genital Herpes Simplex Virus Type 1 and 2 Disease in Mice Immunized with gD-Expressing Dominant-Negative Recombinant HSV-1," *J. Invest. Dermatol.* 129:2470-2479 (2009).

Brans, et al., "Immunization with a Dominant-Negative Recombinant HSV Type 1 Protects against HSV-1 Skin Disease in Guinea Pigs," *J. Invest. Dermatol.* 128:2825-2832 (2008).

Bryson, et al., "Risk of Acquisition of Genital Herpes Simplex Virus Type 2 in Sex Partners of Persons with Genital Herpes: A Prospective Couple Study," *J. Infect. Dis.* 167:942-946 (1993).

Cai, et al., "The Herpes Simplex Virus Type 1 Regulatory Protein ICPO Enhances Virus Replication during Acute Infection and Reactivation from Latency," *J. Virol.* 67(12):7501-7512 (Dec. 1993).

Cai, et al., "The Herpes Simplex Virus Type 1 ICPO Plays a Critical Role in the De Novo Synthesis of Infectious Virus following Transfection of Viral DNA," *J. Virol.* 63(11):4579-4589 (Nov. 1989).

Cohen, et al., "Localization and Synthesis of an Antigenic Determinant of Herpes Simplex Virus Glycoprotein D That Stimulates the Production of Neutralizing Antibody," *J. Virol.* 49(1):102-108 (Jan. 1984).

Coleman, et al., "Determination of Herpes Simplex Virus Type-Specific Antibodies by Enzyme-Linked Immunosorbent Assay," *J Clin. Microbiol.* 18(2):287-291 (Aug. 1983).

Cooper, et al., "Epitope mapping of full-length glycoprotein D from HSV-2 reveals a novel CD4$^+$ CTL epitope located at the transmembrane-cytoplasmic junction," *Cell Immunol.* 239:113-120 (2006).

Corey, et al., "Infections With Herpes Simplex Viruses," *N. Eng. J. Med.* 314:749-757 (1986).

Deluca, et al., "Physical and Functional Domains of the Herpes Simplex Virus Transcriptional Regulatory Protein ICP4," *J. Virol.* 62(3):732-743 (Mar. 1988).

Dolan, et al., "The Genome Sequence of Herpes Simplex Virus Type 2," *J. Virol.* 72(3):2010-2021 (Mar. 1998).

Dudek, et al., "Replication-defective viruses as vaccines and vaccine vectors," *Virology* 344:230-239 (2006).
Fleming, et al., "Herpes Simplex Virus Type 2 in the United States, 1976 to 1994," *N. Eng. J. Med.* 337(16):1105-1111 (1997).
Freeman, et al., "Herpes simplex virus 2 infection increases HIV acquisition in men and women: systematic review and meta-analysis of longitudinal studies," *Aids* 20:73-83 (2006).
Glorioso, et al, "Immunogenicity of Herpes Simplex Virus Glycoproteins gC and gB and Their Role in Protective Immunity," *J. Virol.* 50(3):805-812 (Jun. 1984).
Grammer, et al., "Identification of an HSV-1/HSV-2 Cross-Reactive T Cell Determinant," *J. Immunol.* 145(7):2249-2253 (Oct. 1990).
Gupta, et al., "Genital Herpes," *Lancet* 370:2127-2137 (Dec. 2007).
Handler, et al., "Oligometric Structure of Glycoproteins in Herpes Simplex Virus Type 1," *J Virol.* 70(9):6067-6075 (Sep. 1996).
Hirsch, "Herpes Simplex Virus," p. 1144-1153. In G.L. Mandell, R.G.J. Douglas and J.E. Bennett (ed.), Principles and practice of infectious diseases. Churchill Livingstone Inc., New York (1990).
Honess, et al., "Type Specific and Type Common Antigens in Cells Infected with Herpes Simplex Virus Type 1 and on the Surfaces of Naked and Enveloped Particles of the Virus," *J. gen. Virol.* 22:159-169 (1974).
Hosken, et al., "Diversity of the CD8+ T-Cell Response to Herpes Simplex Virus Type 2 Proteins among Persons with Genital Herpes," *J. Virol.* 80(11):5509-5515 (Jun. 2006).
Johnson, et al., "Herpes Simplex Virus Glycoprotein D is Recognized as Antigen by CD4+ and CD8+ T Lymphocytes from Infected Mice," *J. Immunol.* 145(2):702-710 (Jul. 1990).
Jones, et al., "Vaccination Strategies to Prevent Genital Herpes and Neonatal Herpes Simplex Virus (HSV) Disease," *Herpes* 11(1):12-17 (2004).
Kim, et al., "Immunodominant Epitopes in Herpes Simplex Virus Type 2 Glycoprotein D Are Recognized by CD4 Lymphocytes from Both HSV-1 and HSV-2 Seropositive Subjects," *J. Immunol.* 181:6604-6615 (2008).
Knopf, et al., "Evaluation of the T-REx™ transcription switch for conditional expression and regulation of HSV-1 vectors," *Virus Genes* 36:55-66 (2008).
Koelle, et al., "Herpes Simplex: Insights on Pathogenesis and Possible Vaccines," *Annu. Rev. Med.* 59:381-395 (2008).
Koelle, et al., "Recent Progress in Herpes Simplex Virus Immunobiology and Vaccine Research," *Clin. Microbiol. Rev.* 16(1):96-113 (Jan. 2003).
Koelle, et al., "Prospects for Developing an Effective Vaccine Against Ocular Herpes Simplex Virus Infection," *Curr. Eye Res.* 30:929-942 (2005).
International Search Report for PCT/US07/15540 filed Jul. 6, 2007.
Written Opinion of the International Searching Authority for PCT/US07/15540 filed Jul. 6, 2007.
International Preliminary Report on Patentability for PCT/US2007/15540 filed Jul. 6, 2007.
Advani, et al., "Friendly Fire: Redirecting Herpes Simplex Virus-1 for Therapeutic Applications," *Clin. Microbiol. Infect.* 8:551-563 (2002).
Anderson, W.F., "Human Gene Therapy," *Nature (London)* 392:25-30 (1998).
Clackson, T., "Regulated Gene Expression Systems," *Gene Therapy* 7:120-125 (2000).
Cohen, J., "Bumps on the Vaccine Road," *Science* 265:1371-1373 (Sep. 1994).
Davido, et al., "Role of Cis-Acting Sequences of the ICP0 Promoter of Herpes Simplex Virus Type 1 in Viral Pathogenesis, Latency and Reactivation," *J. General Virology* 77:1853-1863 (1996).
Deuschle, et al., "Tetracycline-Reversible Silencing of Eukaryotic Promoters," *Mol. And Cel. Biol.* 15:1907-1914 (Apr. 1995).
Fox, J.L., "Investigation of Gene Therapy Begins," *Nature Biotechnology* 18:143-144 (Feb. 2000).
Glorioso, et al., "Therapeutic Gene Transfer to the Nervous System Using Viral Vectors," *J. NeuroVirol.* 9:165-172 (2003).
Gossen, et al., "Transcriptional Activation by Tetracyclines in Mammalian Cells," *Science* 268:1766-1769 (Jun. 1995).
Gossen, et al., "Tight Control of Gene Expression in Mammalian Cells by Tetracycline-Responsive Promoters," *Proc. Natl. Acad. Sci. USA* 89:5547-5551 (Jun. 1992).
Hennighausen, et al., "Conditional Gene Expression in Secretory Tissues and Skin of Transgenic Mice Using the MMTV-LTR and the Tetracycline Responsive System," *J Cell. Biochem* 59:463-472 (1995).
Heur, et al., "Tet Repressor-*tet* Operator Contacts Probed by Operator DNA-modification Interference Studies," *J. Mol. Biol.* 202:407-415 (1988).
Hillen, et al., "Mechanisms Underlying Expression of TN*10* Encoded Tetracycline Resistance," *Ann. Rev. Microbiol.* 48:345-369 (1994).
Jacobs, et al., "HSV-1-Based Vectors for Gene Therapy of Neurological Diseases and Brain Tumors: Part I. HSV-1 Structure, Replication and Pathogenesis," *Neoplasia* 1(5):387-401 (1999).
Jacobs, et al., "HSV-1-Based Vectors for Gene Therapy of Neurological Diseases and Brain Tumors: Part II. Vector Systems and Applications," *Neoplasia* 1(5):402-416 (1999).
Kim, et al., "Tetracycline Repressor-Regulated Gene Repression in Recombinant Human Cytomegalovirus," *J. Virol.* 69(4):2565-2573 (1995).
Kmiec, et al., "Investigators Have Been Searching for Ways to Add Corrective Genes to Cells Harboring Defective Genes. A Better Strategy Might be to Correct the Defects," *American Scientist* 87:240-247 (May 1999).
Latchman, et al., "Herpes Simplex Virus Vectors for Gene Delivery to a Variety of Different Cell Types," *Curr. Gene Ther.* 2:415-426 (2002).
Martuza, et al., "Experimental Therapy of Human Glioma by Means of a Genetically Engineered Virus Mutant," *Science* 252:854-856 (1991).
McGeocii, et al., "The Complete DNA Sequence of the Long Unique Region in the Genome of Herpes Simplex Virus Type 1," *J. Gen. Virol.* 69:1531-1574 (1988).
McGeoch, et al., "Complete DNA Sequence of the Short Repeat Region in the Genome of Herpes Simplex Virus Type 1," *Nuc. Acids Res.* 14(4):1727-1745 (1986).
McGeoch, et al., "Comparative Sequence Analysis of the Long Repeat Regions and Adjoining Parts of the Long Unique Regions in the Genomes of Herpes Simplex Viruses Types 1 and 2," *J. Gen. Virol.* 72:3057-3075 (1991).
No, et al., "Ecdysone-Inducible Gene Expression in Mammalian Cells and Transgenic Mice," *Proc. Natl. Acad. Sci. USA* 93:3346-3351 91996).
Palmer, et al., "Development and Optimization of Herpes Simplex Virus Vectors for Multiple Long-Term Gene Delivery to the Peripheral Nervous System," *J. Virol.* 74(12):5604-5618 (Jun. 2000).
Perry, et al., "Characterization of the IE110 Gene of Herpes Simplex Virus Type 1," *J. Gen Virol.* 67:2365-2380 (1986).
Postle, et al., "Nucleotide Sequence of the Repressor Gene of the TN*10* Tetracycline Resistance Determinant," *Nuc. Acids Res.* 12(12):4849-4863 (1985).
Rivera, et al., "A Humanized System for Pharmacologic Control of Gene Expression," *Nature Medicine* 2(9):1028-1032 (1996).
Ross, et al., "Gene Therapy in the United States: A Five-Year Status Report," *Human Gene Therapy* 7:1781-1790 (Sep. 1996).
Scarpini, et al., "Latency Associated Promoter Transgene Expression in the Central Nervous System After Stereotaxic Delivery of Replication-Defective HSV-1-Based Vectors," *Gene Therapy* 8:1057-1071 (2001).
Schmeisser, et al., "Tetracycline-Regulated Gene Expression in Replication-Incompetent Herpes Simplex Virus Vectors," *Hum. Gene Ther.* 13:2113-2124 ( Dec. 2002).
Verma, et al., "Gene Therapy-Promises, Problems, and Prospects," *Nature* 389:239-242 (Sep. 1997).
Wang, et al., "A Regulatory System for Use in Gene Transfer," *Proc. Natl. Acad. Sci. USA* 91:8180-8184 (1994).
Wang, et al., "Mammary Hyperplasia and Carcinoma in MMTV-Cyclin D1 Transgenic Mice," *Nature* 369:669-671 (Jun. 1994).

Wissman, et al., "Saturation Mutagenesis of the Tn*10*-Encoded *tet* Operator $O_1$; Identification of Base-Pairs Involved in Tet Repressor Recognition," *J. Mol. Biol.* 202:397-406 (1988).

Yao, et al., "An Activity Specified by the Osterosarcoma Line U2OS Can Substitute Functionally for ICP0, a Major Regulatory Protein of Herpes Simplex Virus Type 1," *J. Virol.* 69(10):6249-6258 (1995).

Yao, et al., "Tetracycline Repressor, tetR, rather than the tetR-Mammalian Cell Transcription Factor Fusion Derivatives, Regulates Inducible Gene Expression in Mammalian Cells," *Human Gene Ther.* 9:1939-1950 (Sep. 1998).

Yao, et al., "Physical Interaction Between the Herpes Simplex Virus Type 1 Immediate-Early Regulatory Proteins ICP0 and ICP4," *J. Virol.* 68:8158-8168 (1994).

Yao, et al., "Highly Efficient Regulation of Gene Expression by Tetracycline in a Replication-Defective Herpes Simplex Viral Vector," *Mol. Ther.* 13(4):1133-1141 (Jun. 2006).

Appeal Brief filed by Applicant on Nov. 26, 2011 for U.S. Appl. No. 11/117,357.

Examiner's Answer mailed by the USPTO on Feb. 2, 2012 for U.S. Appl. No. 11/117,357.

No, et al., "Ecdysone-Inducible Gene Expression in Mammilian Cells and Transgenic Mice," *Proc. Natl. Acad. Sci. USA* 93:3346-3351 (1996).

* cited by examiner

SEQUENCE LISTING

```
<160> NUMBER OF SEQ ID NOS: 2

<210> SEQ ID NO 1
<211> LENGTH: 19
<212> TYPE: DNA
<213> ORGANISM: Escherichia coli

<400> SEQUENCE: 1
tccctatcag tgatagaga                                              19

<210> SEQ ID NO 2
<211> LENGTH: 48
<212> TYPE: DNA
<213> ORGANISM: Escherichia coli

<400> SEQUENCE: 2
tccctatcag tgatagagat ctccctatca gtgatagaga tcgctgca              48
```

US 8,236,941 B2

TETRACYCLINE REPRESSOR REGULATED ONCOLYTIC VIRUSES

CROSS REFERENCE TO RELATED APPLICATIONS

The present application is a division of U.S. Ser. No. 11/822,373, filed on Jul. 5, 2007, which claims the benefit of U.S. provisional application 60/819,382, filed on Jul. 10, 2006. These prior applications are hereby incorporated by reference in their entirety.

STATEMENT OF GOVERNMENT FUNDING

This invention was made with Government support under Grant Nos. RO1AI05088 and RO1GM51449 awarded by the National Institutes of Health. The U.S. Government therefore has certain rights in the invention.

FIELD OF THE INVENTION

The present invention is concerned with oncolytic viruses, especially Herpes Simplex Virus type 1, that rely upon the tetracycline resistance (tet) operator and repressor to control their replication after the infection of tumor cells and/or normal cells. It encompasses DNA sequences used in recombinantly producing the viruses and methods in which the viruses are used in the treatment of cancer patients.

BACKGROUND OF THE INVENTION

Oncolytic viruses are designed to infect and destroy cancer cells, while leaving normal cells relatively unaffected (MacLean et al., *J. Gen. Virol.* 72:630-639 (1991); Robertson et al., *J. Gen. Virol.* 73:967-970 (1992); Brown et al., *J. Gen. Virol.* 75:3767-3686 (1994); Chou et al., *Science* 250:1262-1265 (1990)). One virus that has been of particular interest as an oncolytic is Herpes simplex virus-1 (HSV). HSV can infect a broad range of cell types and has large genome, which allows multiple therapeutic genes to be packaged into recombinants. Experimental evidence for the antitumor effect of HSV against gliomas has existed for over a decade (Martuza, et al., *Science* 252:854-856 (1991); see also: Mineta et al., *Nature Med.* 1:938-943 (1995); Market et al., *J. Neurosurg.* 77:590-594 (1992); Randazzo et al., *Virology* 211:94-101 (1995); Kesari et al., *Lab. Invest.* 73:636-648 (1995)) and more recent studies suggest that it should be effective for the treatment of tumors of the lung, liver and ovary as well (U.S. Pat. No. 6,428,968; see also Montgomery et al., *Cell* 87:427-436 (1996)). Unfortunately, attempts to develop viruses that only target or replicate in cancer cells while maintaining their cytolytic effectiveness has met with only limited success. For example, it has been found that the deletion of genes that impair viral replication in normal cells also leads to a significant decrease in the oncolytic activity of the virus in targeted tumor cells (Kramm, et al. *Hum. Gene Ther.* 8(17):2057-68 (1997); Advani, et al., *Gene Ther* 5(2):160-165 (1998); Chung, et al., *J. Virol.* 73(9):7556-64 (1999)).

Thus, it remains a great challenge to construct an oncolytic HSV recombinant that offers a high degree of safety while its replication capability in tumor cells remains at levels close to that of a wild-type virus. In principle, this can be achieved if one can construct an oncolytic recombinant virus whose de novo replication can be tightly controlled and adjusted by a pharmacological agent in the localized tumor microenvironment. This virus should minimize concerns regarding the potential unwanted spread of oncolytic virus to other tissues, prevent overloads of progeny oncolytic viruses at the end of tumor killing and quickly shut down the oncolytic activity of the virus if unwanted adverse effects are detected in a patient.

Recently, a tetracycline-inducible transcription switch for use in mammalian cells was developed (U.S. Pat. No. 6,444,871; Yao, et al., *Hum. Gene Ther.* 9:1939-1950 (1998)) and used to adapt HSV as a vector for delivering therapeutic genes to cells (US published application 2005-0266564). However, it has not been clear whether this degree of regulation is sufficient in controlling de novo replication of an oncolytic virus or whether it is possible to develop a safe and effective therapy that does not rely on viruses being highly specific for cancer cells.

SUMMARY OF THE INVENTION

The present invention is based upon the use of a tet operator/repressor system for controlling the replication of oncolytic viruses. Control is achieved by putting the expression of a gene needed for viral replication under the control of the tet operator and expressing large amounts of tet repressor either before, or soon after, cells are infected. The repressor binds to the operator, thereby preventing gene transcription and blocking viral replication. If tetracycline is introduced into the system, it binds to the repressor and causes it to disassociate from the operator. As a result, gene transcription is permitted, virus replication proceeds and, ultimately, this leads to the lysis of the host cell.

Lysis of cancer cells using the viruses described herein appears to trigger an immune response against tumor-associated antigens. Thus, in addition to relying upon the direct oncolytic effects of virus to destroy infected cancer cells, the present invention also depends upon the subsequent action of the immune system to induce a specific host immune response against cancer cells. Damage to non-cancer cells is minimized by applying virus directly to tumors and then inducing virus replication by applying tetracycline for a limited time and/or in a localized tumor microenvironment. Once the tetracycline is removed (or in tissues that have limited access to tetracycline, i.e., when tetracycline or its derivatives are introduced into a localized tumor microenvironment), the virus is no longer able to replicate to a significant extent and therefore its spread to non-cancerous cells is minimized.

In its first aspect, the invention is directed to a recombinant DNA molecule that includes a promoter sequence with a TATA element. The promoter is under the control of a tetracycline operator sequence that has two op2 repressor binding sites joined together by between two and twenty linking nucleotides. The positioning of the operator sequence is important to achieve effective control over the promoter. Specifically, the first nucleotide in the operator sequence must be located between six and twenty-four nucleotides 3' to the last nucleotide in the TATA element. In addition, the recombinant DNA molecule includes a gene necessary for viral Herpes simplex virus 1 (referred to herein as HSV-1 or, unless otherwise indicated expressly or by context, HSV) or Herpes simplex virus 2 (referred to herein as HSV-2) replication that lies 3' to the tet operator and which is operably linked to the promoter. The term "operably linked" refers to genetic elements that are joined together in a manner that enables them to carry out their normal functions. For example, a gene is operably linked to a promoter when its transcription is under the control of the promoter and this transcription results in the production of the product normally encoded by the gene. The term "recombinant" refers to a nucleic acid that is formed by experimentally recombining nucleic acid sequences and sequence elements. A recombinant host cell would be a cell that has received a recombinant nucleic acid.

Preferably, the gene necessary for viral replication in the recombinant DNA described above is a gene essential for the replication of Herpes simplex virus-1 (HSV) and the gene can be an essential immediate-early gene, e.g., ICP4 and ICP27, or an essential early or late gene, e.g., ICP8, UL9, and VP5. In addition, the recombinant DNA molecule may include a ribozyme sequence lying in the 5' untranslated region of the essential gene and a second promoter operably linked to a sequence encoding the tet repressor. The ribozyme will help to ensure low level of expression of the essential gene immediately after infection of cells, especially, if the viral essential immediate-early gene is used. Preferable promoters for direct expression of tet repressor in the recombinant DNA molecules are either the HSV immediate-early promoters or the hCMV major immediate-early promoter.

In another aspect, the invention is directed to an oncolytic virus that comprises any of the recombinant DNA molecules described above. The virus must have a genome in which there is: a) a first promoter sequence having a TATA element; b) a tetracycline operator sequence comprising two op2 repressor binding sites joined by 2-20 linking nucleotides, wherein the first nucleotide in the tet operator is between 6 and 24 nucleotides 3' to the last nucleotide in the TATA element; and c) a gene necessary for virus replication lying 3' to the operator and operably linked to the first promoter. It should preferably also include: d) at least one sequence encoding a tet repressor and under the control of a second promoter. The term "second promoter" means that the sequence encoding the tet repressor is not under the control of the same promoter as the gene needed for viral replication, although the same type of promoter may be used in each case. For example there may be two ICP27 promoters, one operably linked to the gene needed for viral replication and one to the sequence encoding the tet promoter, but there should not be a single promoter operably linked to both.

The oncolytic virus is preferably HSV and is produced using standard methodology well-known in the art of virology. Preferred promoters are the HSV immediate early promoters for directing expression of tet repressor, and the preferred promoters and genes needed for virus replication are the HSV essential immediate-early, early and late genes. It is also preferred that the virus have two tet repressor sequence elements present, each under the control of an immediate early promoter. In addition a ribozyme sequence may be present in the 5' untranslated region of the gene needed for viral replication. Other viruses with these elements present are also part of the invention with the next most preferred being adenovirus.

The invention also includes methods of treating cancer patients having a solid tumor by locally administering the oncolytic viruses described herein. The term "locally administering" means that the virus is applied directly to the tumor itself, e.g., by injection, infusion, or, in the case of certain skin cancers, topical administration. In order for the therapy to be effective, cancer cells must be treated so that they have two characteristics. First, they must be infected with a virus whose replication can be controlled by tetracycline and its derivatives. This is accomplished by infecting the cancer cells with a virus, preferably HSV, that has, as described above, at least the following elements: a) a first promoter sequence having a TATA sequence; b) a tetracycline operator sequence comprising two op2 repressor binding sites joined by 2-20 linking nucleotides, wherein the first nucleotide in the tet operator is between 6 and 24 nucleotides 3' to the last nucleotide in said TATA element; and c) a gene necessary for virus replication lying 3' to the operator and operably linked to the first promoter.

The second characteristic that the cells must have is that they must also make the tet repressor. This can be accomplished using a single virus which, in addition to elements a-c, also includes a sequence encoding the tet repressor operably linked to a second promoter. However, other ways of modifying the cancer cells to express the tet repressor may also be used. For example, the cells may first be infected with a different virus expressing the tet repressor or transformed with an expression vector, e.g., a plasmid, that leads to expression of repressor, and then subsequently infected with a virus having elements a-c. Many variations on this scheme will be readily apparent to those of skill in the art but the ultimate objective of treating cancer cells so that they have a virus whose replication is controlled by the tet operator and so that they also produce the tet repressor will always be the same.

The amount of virus administered will vary from patient to patient but it is generally expected that between $1 \times 10^6$ and $1 \times 10^{10}$ PFU (plaque forming units) will be administered at a time. Tetracycline will be administered either systemically to the patient or, more preferably, locally to the tumor either at the time of infection or 1 to 72 h prior to infection. The administration of tetracycline will have the effect of allowing de novo viral replication, leading to synthesis of progeny virus, cell lysis, and subsequent intratumoral spread of newly synthesized virus within the tumor. This method may be used for the treatment of any type of solid tumor including tumors of the lung, colon, brain, breast, prostate, pancreas, kidney, esophagus, liver, ovary, testis and stomach. Melanomas may also be treated using the method.

The procedures for treating cancer by administering oncolytic viruses described herein may be combined with any other treatments that are common in the art including surgery, radiation therapy, and chemotherapy. In addition, the administration of virus may be repeated based upon the clinical judgment of the attending physician. Finally, since it is believed that one of the main actions of the virus will be mediated by an activation of the host immune system against tumor antigens released as a result of lysis, other agents designed to boost a patient's immune response may also be administered or incorporated into the above described recombinant virus.

DETAILED DESCRIPTION OF THE INVENTION

The present invention is based upon the discovery that the tet operator/repressor system can be used to tightly regulate the replication of an HSV oncolytic virus. After infecting tumor cells, the introduction of tetracycline produced a 1000 to 30,000 fold increase in virus replication. In addition to directly lysing infected cells, the virus also inhibits the growth of tumor in immuno-competent mice at a different site from the site of infection. This suggests that cell lysis induced by the virus causes an immune response against tumor specific antigens. While not being held to any particular theory, it is believed that the virus contributes to this response both by making antigen more available due to cell lysis and by somehow inducing a stronger response, i.e., acting in a manner analogous to an adjuvant. The methods discussed below are described primarily with reference to the HSV-1 virus but it will be readily apparent to one of skill in the art that they may be also applied to other viruses, e.g., adenovirus.

The Tet Operator/Repressor Switch and Recombinant DNA

The present invention is directed to, inter alia, oncolytic viruses whose replication is regulated using the tetracycline operator and repressor protein (for sequences see Postle et al., *Nucl. Acid Res.* 12:4849-4863 (1984); Hillen et al., *Ann. Rev. Microbiol.* 48:345-369 (1994); Wissmann et al., *J. Mol. Biol.* 202:397-406 (1988)). General methods for making recombinant DNA molecules containing these elements and DNA sequences have been previously described (see U.S. Pat. No. 6,444,871) and plasmids which contain the tetracycline-inducible transcription switch are commercially available (T-REx™, Invitrogen, CA). An example of a specific method for viral construction is provided below in the Examples section but many alternatives will be readily apparent to one of skill in the art.

An essential feature of the DNA of the present invention is the presence of a gene needed for virus replication that is operably linked to a promoter having a TATA element. A tet operator sequence is located between 6 and 24 nucleotides 3' to the last nucleotide in the TATA element of the promoter and 5' to the gene. The strength with which the tet repressor binds to the operator sequence is enhanced by using a form of operator which contains two op2 repressor binding sites (each such site having the nucleotide sequence: TCCCTATCAGTGATAGAGA (SEQ ID NO:1)) linked by a sequence of 2-20, preferably 1-3 or 10-13, nucleotides. When repressor is bound to this operator, very little or no transcription of the associated gene will occur. If DNA with these characteristics is present in a cell that also expresses the tetracycline repressor, transcription of the gene will be blocked by the repressor binding to the operator and replication of the virus will not occur. However, if tetracycline is introduced, it will bind to the repressor, cause it to dissociate from the operator, and virus replication will proceed.

Selection of Promoters and Genes

During productive infection, HSV gene expression falls into three major classes based on the temporal order of expression: immediate-early ($\alpha$), early ($\beta$), and late ($\gamma$), with late genes being further divided into two groups, $\gamma 1$ and $\gamma 2$. The expression of immediate-early genes does not require de novo viral protein synthesis and is activated by the virion-associated protein VP16 together with cellular transcription factors when the viral DNA enters the nucleus. The protein products of the immediate-early genes are designated infected cell polypeptides ICP0, ICP4, ICP22, ICP27, and ICP47 and it is the promoters of these genes that are preferably used in directing the expression of tet repressor (tetR). The expression of a gene needed for virus replication is under the control of the tetO-containing promoters and these essential genes may be immediate-early, early or late genes, e.g., ICP4, ICP27, ICP8, UL9, gD and VP5.

ICP0 plays a major role in enhancing the reactivation of HSV from latency and confers a significant growth advantage on the virus at low multiplicities of infection. ICP4 is the major transcriptional regulatory protein of HSV-1, which activates the expression of viral early and late genes. ICP27 is essential for productive viral infection and is required for efficient viral DNA replication and the optimal expression of viral $\gamma$ genes and a subset of viral $\beta$ genes. The function of ICP47 during HSV infection appears to be to down-regulate the expression of the major histocompatibility complex (MHC) class I on the surface of infected cells.

Inclusion of Tet Repressor and Making of Virus

The recombinant DNA may also include at least one, and preferably at least two, sequences coding for the tetracycline repressor with expression of these sequences being under the control of an immediate early promoter, preferably either an ICP0 or ICP4 promoter. The sequences for the HSV ICP0 and ICP4 promoters and for the genes whose regulation they endogenously control are well known in the art (Perry, et al., *J. Gen. Virol.* 67:2365-2380 (1986); McGeoch et al., *J. Gen. Virol.* 72:3057-3075 (1991); McGeoch et al., *Nucl. Acid Res.* 14:1727-1745 (1986)) and procedures for making viral vectors containing these elements have been previously described (see US published application 2005-0266564). These promoters are not only very active in promoting gene expression, they are also specifically induced by VP16, a transactivator released when HSV-1 infects a cell. Thus, transcription from ICP0 or ICP4 is particularly high when repressor is most needed to shut down virus replication.

Once appropriate DNA constructs have been produced, they may be incorporated into HSV-1 virus using methods that are well known in the art. One appropriate procedure is described in US 2005-0266564 but other methods known in the art may also be employed.

Treatment Methods

The oncolytic viruses described herein will be applied directly to tumors. In cases where tumors are readily accessible, e.g., tumors of the skin, mouth or which are accessible as the result of surgery, virus can be applied topically. In other cases, it can be administered by injection or infusion. The tetracycline used prior to infection or at a time of infection can also be administered in this way or it can be administered systemically.

Prior to administration, the oncolytic viruses can be suspended in any pharmaceutically acceptable solution including sterile isotonic saline, water, phosphate buffered saline, 1,2-propylene glycol, polyglycols mixed with water, Ringer's solution, etc. The exact number of viruses to be administered is not crucial to the invention but should be an "effective amount," i.e., an amount sufficient to cause cell lysis extensive enough to generate an immune response to released tumor antigens. Since virus is replicated in the cells after infection, the number initially administered will increase rapidly with time. Thus, widely different amounts of initially administered virus can give the same result by varying the time that they are allowed to replicate, i.e., the time during which cells are exposed to tetracycline. In general, it is expected that the number of viruses (PFU) initially administered will be between $1\times10^6$ and $1\times10^{10}$.

Tetracycline will be administered either locally or systemically to induce viral replication at a time of infection or 1-72 h prior to infection. The amount of tetracycline to be administered will depend upon the route of delivery. In vitro, 1 ug/ml of tetracycline is more than sufficient to allow viral replication in infected cells. Thus, when delivered locally, a solution containing anywhere from 0.01 ug/ml to 100 ug/ml may be administered. However, much higher doses of tetracycline (e.g., 10-500 mg/ml) can be employed if desired. The total amount given locally at a single time will depend on the size of the tumor or tumors undergoing treatment but in general, it is expected that between 0.5 and 200 ml of tetracycline solution would be used at a time. When given systemically, higher doses of tetracycline will be given but it is expected that the total amount needed will be significantly less than that typically used to treat bacterial infections (usually 1-2 grams per day in adults divided into 2-4 equal doses and, in children, 10-20 mg per pound of body weight per day). It is expected that 100-200 mg per day should be effective in most cases.

The effectiveness of a dosage, as well as the effectiveness of the overall treatment can be assessed by monitoring tumor size using standard imaging techniques over a period of days, weeks and/or months. A shrinkage in the size or number of tumors is an indication that the treatment has been successful. If this does not occur or continue, then the treatment can be repeated as many times as desired. In addition, treatment with virus can be combined with any other therapy typically used for solid tumors, including surgery, radiation therapy or chemotherapy. In addition, the procedure can be combined with methods or compositions designed to help induce an immune response.

EXAMPLES

The current example describes the creation and testing of an oncolytic HSV-1 recombinant, KTR-27, which encodes two copies of the tetR gene controlled by the HSV-1 immediate-early ICP0 promoter in the ICP0 locus and the essential ICP27 gene under the control of the tetO-bearing ICP27 promoter. To reduce the levels of ICP27 expression immediately after HSV infection, a riboenzyme sequence was inserted at the 5' untranslated region of ICP27. Alternative designs and methods will be readily apparent to those of skill in the art.

Materials and Methods

Plasmids p27BS is an ICP27-expressing plasmid with flanking sequences 406 bp upstream of the ICP27 open-reading frame to 461 bp downstream of ICP27 poly A signal ptetO27, derived from p27BS, contains two tandem tet operators (5'-TCCCTATCAGTGATAGAGATCTCCCTATCAGTGATA-GAGATCGCTGCA-3' (SEQ ID NO:2)) at 20 bp downstream of the last nucleotide of the TATAAGG element of the ICP27 promoter. Note that the tet operator consists of two op2 repressor binding sites joined by the 2 nucleotide sequence TC. Insertion of a DNA sequence containing the mentioned tetO elements (underlined text) at the Eag I site downstream of the ICP27 TATA element in the described orientation generates a unique Eag I site at the 5' end of the insert and a unique Pst I site at the 3' end of the insert. Using lacZ as a reporter, we demonstrate that, like the tetO-bearing hCMV major immediate-early promoter, the tetO-bearing ICP27 promoter can be sensitively regulated by tetracycline in the presence of tetR.

ptetORZ27, derived from ptetO27, contains a DNA sequence encoding a self-cleavage ribozyme N107 (Yen, et al., *Nature* 431:471-476 (2004)), flanked with 5' Pst 1 and 3' Age I sequences, into the 5' untranslated region of ICP27 coding sequence of ptetO27 at the Pst I and Age I sites. Presence of tetO and N107 sequences in ptetORZ27 was verified by DNA sequencing. Western blot analysis of cell extracts prepared from ptetO27 and ptetORZ27 transfected U2OS cells demonstrate that the presence of N107 in ptetORZ27 significantly reduced levels of ICP27 expression in ptetORZ27-transfected cells.

Cells and Viruses

Osteosarcoma line U2OS, African green monkey kidney (Vero) cells were grown in Dulbecco's modified Eagle's medium (DMEM) supplemented with 10% fetal bovine serum (FBS) (Yao, et al., *J Virol* 69(10):6249-6258 (1995)). U2OS cells encode a cellular function that can complement the function of the HSV-1 immediate-early regulatory protein ICP0. Human embryonic lung cells, HEL638 were grown in DMEM in the presence of 10% FBS plus 1× non-essential amino acid (Sigma). R27 is an ICP27 expressing cell line derived from tetR-expressing U2OS cells (Augustinova, et al., *J. Virol.* 78(11):5756-65 (2004)). R27 cells were grown in DMEM growth medium in the presence of G418 (400 ug/ml) and hygromycin B (50 ug/ml).

Human Non-Small cell lung cancer cells H1299, human breast cancer cells MCF7, human prostate cancer cells PC1435, and pancreatic cancer cells Pan 1 were cultured in DMEM containing 10% FBS. Mouse melanoma cells M3 were grown in Kaighan's modification of Ham's F12 medium supplemented with 15% horse serum and 2.5% FBS.

7134 is an ICP0 null mutant, in which both copies of the ICP0 coding sequence are replaced by the Lac Z gene of *Escherichia coli* (Cai, et al., *J. Virol.* 63(11):4579-(1989)). 7134 was propagated and assayed in U2OS cells ((Yao, et al., *J. Virol.* 69(10):6249-6258 (1995)). KOR is an HSV-1 recombinant that was generated by recombinational replacement of the Lac Z genes of 7134 with DNA sequence-encoding tetR (Yao et al., *Mol. Ther.* 13(6):1133-41 (2006)). K0R27-lacZ was derived from KOR in which the ICP27 coding sequence was replaced by the lacZ gene by homologous recombination. K0R27-lacZ is replication-defective in U2OS cells, and was propagated and assayed in R27 cells.

Construction of KTR27

KTR27 was constructed by replacing the Lac Z gene of K0R27-lacZ with the ribozyme-containing ICP27 gene under the control of the tetO-bearing ICP27 promoter. In brief, we transfected U2OS cells with linearized ptetORZ27 DNA followed by K0R27-lacZ super-infection. Progeny viruses were harvested at 24 h post-infection and plaque assayed on U2OS cell monolayers in the presence of tetracycline. Plaques, indicating replacement of the lacZ gene by the ICP27 gene, were isolated and plaque purified four times on U2OS cell monolayer in the presence of tetracycline. KTR27 is a viral recombinant that is replication-competent in the presence of tetracycline and replication impaired in the absence of tetracycline in both Vero and U2OS cells.

Regulation of De Novo Viral Replication in Vero Cells

Vero cells were seeded at $7.5 \times 10^5$ cells per 60-mm dish. At about 24 h post-seeding, cells in triplicate dishes were infected with KTR-27 at a multiplicity of infection (MOI) of 1 PFU/cell in a volume of 0.5 ml. After 1.5 h incubation at 37° C., virus-containing inoculation medium was removed, and cells were washed twice with acid-glycine saline followed by two more washes with DMEM. Infections were then carried out either in the absence or presence of 2.5 µg/ml of tetracycline. Infected cells were harvested at 24, 48, and 72 h post-infection, respectively. Viral titers were determined by standard plaque assay on U2OS cell monolayer in the presence of tetracycline.

Regulation of Viral Replication in Human Cancer Cells

Viral replication was examined in the human cancer cells PC1435 (prostate), H1299 (lung), MCF7 (breast), and Panc 1 (pancreas). PC1435, H1299, MCF7, and Panc 1 cells were seeded at $5 \times 10^5$ cells per 60-mm dish. At 48 h post-seeding, cells in triplicate dishes were infected with KTR-27 at an MOI of 1 PFU/cell in a volume of 0.5 ml. After 1.5 h incubation at 37° C., inoculation medium was removed followed by two washes with acid-glycine saline, then with DMEM. Infections were carried out in the absence or presence of tetracycline at 2.5 µg/ml. Infected cells were harvested at 72 h post-infection and viral titers were determined by standard plaque assay on U2OS cell monolayer in the presence of tetracycline.

Regulation of Viral Replication in Human Embryonic Lung Cells

Tetracycline-dependent de novo viral synthesis of KTR-27 was examined in primary human embryonic lung cells (HEL638). HEL cells were seeded at $7.5 \times 10^5$ cells per 60-mm dish. At about 48 h post-seeding, cells in triplicate dishes were infected with KTR-27 at an MOI of 1 or 3 PFU/cell in the absence or presence of 2.5 µg/ml of tetracycline as described above. Infected cells were harvested at 48 h post-infection for cells that were infected at an MOI of 3 PFU/cell and at 72 h post-infection for cells infected at an MOI of 1 PFU/cell. Viral titers were determined on U2OS cell monolayer in the presence of tetracycline.

Dose Dependent Regulation

Tetracycline dose-dependent regulation of de novo viral synthesis of KTR27 in Vero cells. Vero cells were seeded at $5 \times 10^5$ cells per 60-mm dish. At 48 h post-seeding, cells in triplicate dishes were infected with KTR27 at an MOI of 1 PFU/cell in the absence or presence of tetracycline at concentrations of 0.01, 0.05, 0.5 and 2.5 µg/ml, respectively. Infected cells were harvested at 72 h post-infection and viral titers were determined on U2OS cell monolayer in the presence of tetracycline.

Test of Effectiveness in an In Vivo Model of Non-Small Cell Lung Cancer

Female BALB/c (nu/nu), 6 to 8-weeks-old, were implanted s.c. with $7.5 \times 10^6$ human lung cancer cells H1299 in a volume of 100 ul at the left and right flanks. Once mice developed palpable tumors, they were randomly divided intro three groups, and one group was started on doxycycline-containing diet. Three days later, each tumor with a maximum diameter of 4-5 mm was injected with 50 µl of DMEM or KTR27 at a dose of $1 \times 10^7$ PFU. The inoculated tumors received identical treatment 3 and/or 7 days later. For the group of mice treated with doxycycline, doxycycline special diet was discontinued 6 days after the first virus inoculation. Tumor volumes were quantified every third day using the formula $V=(L \times (W)^2)/2$ for 24 days.

Effectiveness in a Syngeneic M3 Melanoma Model in Immuno-Competent Mice

Female DBA/2 mice, 6 to 8-weeks-old, were implanted s.c. with $1 \times 10^5$ syngeneic M3 Cloudman melanoma cells in a volume of 100 µl at both the left and right flanks. When subcutaneous tumors reached a palpable size, mice were randomly divided intro three groups of 6 mice each and one group was started on Doxycycline special diet. Three days later (maximum diameter of tumor size: 4-5 mm), mice were anesthetized and received a single intratumoral inoculation of KTR-27 at $5 \times 10^7$ PFU or DMEM in a volume of 50 ul unilaterally. Mice were fed ad libitum either a standard diet or a doxycycline-containing diet. Doxycyline special diet was discontinued 5 days after virus inoculation and henceforth all mice received a normal diet throughout the experiment. Volumes of injected and contralateral tumors were quantified every third day by a caliper using the formula $V=(L \times (W)^2)/2$ until 21 days after treatment. Mean tumor volumes±SEM were calculated.

Results

Regulation of Viral Replication in Cultured Cells

A greater than 150,000-fold of tetracycline-dependent de novo viral production was detected in African green monkey kidney (Vero) cells. Infection of human tumor cell lines, such as breast, lung, prostate, and pancreatic tumors, with KTR-27 in the presence of tetracycline led to 1000- to 30,000-fold higher progeny viral production than that produced in cells infected in the absence of tetracycline. Similarly effective regulation of KTR-27 viral production by tetracycline was also seen in proliferating primary human embryonic lung cells. Moreover, it was found that the degree of de novo replication of KTR-27 can be adjusted by tetracycline in a dose-dependent fashion.

Safety of In Vivo Injection

In order to examine the safety of KTR27 in a potential clinical application, the neurovirulence of KTR-27 after intracerebral inoculation was tested. Female CD-1 mice, 6 to 8-weeks-old, were randomly assigned to three groups and anesthetized with sodium pentobarbital. Groups of mice were fed either a normal diet (n=7) or a diet containing doxycycline (n=8). After 3 days of feeding, mice were inoculated with KTR27 through intracerebral injection into the left frontal lobe of the brain in a volume of 10 µl ($1 \times 10^7$ PFU) at a depth of 4.5 mm. As a negative control, a group of mice received intracerebral injection of DMEM (n=4) in a similar fashion. Mice were examined for signs and symptoms of illness for 35 days after KTR27 inoculation. It was found that all mice behaved normally and did not display any symptoms of disease over this period.

Effectiveness in an In Vivo Model of Non-Small Cell Lung Cancer

We examined the direct oncolytic effect of KTR27 in killing human tumors in a pre-established mouse tumor xenograft model of pre-established subcutaneous human non-small-cell lung cancer in nude mice in either the presence or absence of tetracycline treatment. It was found that intratumoral inoculation of KTR27 significantly inhibited the growth of established lung tumor compared to DMEM treated control. After 24 days, tumor volume in mice receiving a standard rodent diet and inoculated with KTR27 was less than half of the tumor volume in the DMEM control mice. For mice receiving the doxycycline diet, tumor volume after 24 days was less than ten percent the tumor volume in the DMEM control mice. No toxic effects or signs of herpetic infection were observed in surrounding normal tissue following intratumoral injection of KTR27 in the tetracycline-fed mice.

Effectiveness in a Syngeneic M3 Melanoma Model in Immuno-Competent Mice

The therapeutic treatment of established bilateral tumors in DBA/2 mice was examined. It was found that intratumoral inoculation of KTR-27 into pre-established melanoma lead to little measurable growth in KTR-27 treated tumors, while tumors that received a DMEM injection grew more than 100-fold in size. It was found that KTR-27 can also provide a potent anti-tumor effect on contralateral tumors that received no viruses, suggesting that intratumoral inoculation of KTR27 can elicit a strong effective anti-tumor specific immunity. No difference in tumor killing efficiency was observed in mice that received doxycycline diet or standard rodent diet, which can likely be explained by the inefficient replication of KTR-27 in M3 cells in the presence of tetracycline and rapid cytotoxicity induced by KTR27 infection of M3 cells in the absence of tetracycline. We observed that infection of M3 cells with KTR27 at an MOI of 3 PFU/cell led to about 100% cells detached from dishes in both the presence and absence of tetracycline, and virus yield at 24 h post-infection in the presence of tetracycline was only 0.21 PFU/cell. Again, no signs of herpetic infection were observed on surrounding normal tissue following intratumoral injection of KTR-27.

CONCLUSIONS

In summary, we have developed an oncolytic HSV recombinant whose de novo viral replication can be sensitively regulated by tetracycline in normal replicating cells and various tumor cells. KTR-27 is highly effective and safe against pre-established non-small cell lung cancer in nude mice and can prevent the growth of pre-established M3 mouse melanoma in immuno-competent mice. Intratumoral inoculation of KTR-27 can elicit a systemic immune response that can effectively prevent the growth of a distant tumor in immuno-competent mice.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A recombinant DNA molecule, comprising:
   a) a first promoter sequence having a TATA element;
   b) a tetracycline operator sequence comprising two op2 repressor binding sites joined by 2-20 linking nucleotides, wherein the first nucleotide in said tet operator is between 6 and 24 nucleotides 3' to the last nucleotide in said TATA element; and
   c) a gene having a 5' untranslated region, wherein said gene:
      i) is necessary for Herpes simplex virus 1 (HSV-1) or Herpes simplex virus 2 (HSV-2) replication,
      ii) lies 3' to said operator; and
      iii) is operably linked to said first promoter;
   d) a ribozyme sequence capable of reducing the translation of said gene and located in said 5' untranslated region of said gene.

2. The recombinant DNA of claim 1, wherein said gene is necessary for HSV-1 replication.

3. The recombinant DNA of claim 2, wherein said first promoter is an immediate early promoter.

4. The recombinant DNA of claim 2, wherein said first promoter is selected from the group consisting of: the ICP4 promoter; ICP27 promoter; ICP8 promoter; UL9 promoter; gD promoter; and VP5 promoter.

5. The recombinant DNA of claim 2, wherein said gene necessary for viral replication is ICP27, ICP4, ICP8, UL9, gD, or VP5.

6. The recombinant DNA of claim 2, wherein;
   a) said promoter is an HSV-1 ICP27 promoter and said gene necessary for viral replication is ICP27;
   b) said promoter is an ICP4 promoter and said gene necessary for viral replication is ICP4;
   c) said promoter is an HSV-1 ICP8 promoter and said gene necessary for viral replication is ICP8;
   d) said promoter is an HSV-1 UL9 promoter and said gene necessary for viral replication is UL9;
   e) said promoter is an HSV-1 gD promoter and said gene necessary for viral replication is gD; or
   f) said promoter is a VP5 promoter and said gene necessary for viral replication is VP5.

7. The recombinant DNA of claim 6, wherein said DNA has at least one sequence encoding the tet repressor under the control of a second promoter.

8. The recombinant DNA of claim 7, wherein said second promoter is an HSV-1 immediate early promoter, or the hCMV major immediate-early promoter.

9. The recombinant DNA of claim 1, wherein said recombinant DNA is part of the HSV-2 genome.

10. The recombinant DNA of claim 1, wherein said recombinant DNA is part of the HSV-1 genome.

11. An oncolytic virus with a genome comprising the recombinant DNA of claim 1.

12. The oncolytic virus of claim 11, wherein said gene in said recombinant DNA is necessary for HSV-1 replication and said first promoter in said recombinant DNA is an HSV-1 promoter selected from the group consisting of: the ICP4 promoter; ICP27 promoter; ICP8 promoter; UL9 promoter; gD promoter; and VP5 promoter.

13. The oncolytic virus of claim 12, wherein said gene in said recombinant DNA is an HSV-1 gene selected from the group consisting of: ICP27, ICP4, ICP8, UL9, gD, or VP5.

14. The oncolytic virus of claim 13, wherein;
   a) said promoter is an ICP27 promoter and said gene necessary for viral replication is ICP27;
   b) said promoter is an ICP4 promoter and said gene necessary for viral replication is ICP4;
   c) said promoter is an ICP8 promoter and said gene necessary for viral replication is ICP8;
   d) said promoter is a UL9 promoter and said gene necessary for viral replication is UL9;
   e) said promoter is a gD promoter and said gene necessary for viral replication is gD; or
   f) said promoter is a VP5 promoter and said gene necessary for viral replication is VP5.

15. An oncolytic virus with a genome comprising:
   a) a first promoter sequence having a TATA element;
   b) a tetracycline operator sequence comprising two op2 repressor binding sites joined by 2-20 linking nucleotides, wherein the first nucleotide in said tet operator is between 6 and 24 nucleotides 3' to the last nucleotide in said TATA element; and
c) an HSV-1 gene having a 5' untranslated region, wherein said gene:
   i) is selected from the group consisting of: ICP27, ICP4, ICP8, UL9, gD, and VP5;
   ii) lies 3' to said operator; and
   iii) is operably linked to said first promoter;
d) a ribozyme sequence capable of reducing the translation of said gene and located in said 5' untranslated region of said gene; and
e) at least one sequence encoding the tet repressor under the control of a second promoter.

16. The oncolytic virus of claim 15, wherein said first promoter is an HSV-1 promoter selected from the group consisting of: the ICP4 promoter; ICP27 promoter; ICP8 promoter; UL9 promoter; gD promoter; and VP5 promoter.

17. The oncolytic virus of claim 16, wherein;
a) said first promoter is the ICP27 promoter and said gene is ICP27;
b) said first promoter is ICP4 and said gene is ICP4;
c) said first promoter is ICP8 and said gene is ICP8;
d) said first promoter is UL9 and said gene necessary is UL9;
e) said first promoter is gD and said gene is gD; or
f) said first promoter is VP5 and said gene is VP5.

18. The oncolytic virus of claim 17, wherein said second promoter is the HSV-1 ICP0 promoter.

19. The oncolytic virus of claim 18, wherein said first promoter is the ICP27 promoter and said gene is ICP27.

20. The oncolytic virus of claim 19, wherein said recombinant DNA does not include a functional ICP6 gene or does not include a functional ICP47 gene.

* * * * *